(12) United States Patent
McCabe et al.

(10) Patent No.: US 7,696,191 B2
(45) Date of Patent: *Apr. 13, 2010

(54) CRYSTALLINE COMPOUND

(75) Inventors: James McCabe, Macclesfield (GB); Gary Peter Tomkinson, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 11/962,838

(22) Filed: Dec. 21, 2007

(65) Prior Publication Data

US 2008/0153800 A1 Jun. 26, 2008

Related U.S. Application Data

(60) Provisional application No. 60/871,255, filed on Dec. 21, 2006.

(51) Int. Cl.
| | |
|---|---|
| *A01N 43/00* | (2006.01) |
| *A61K 31/397* | (2006.01) |
| *A61K 31/00* | (2006.01) |
| *A01N 43/58* | (2006.01) |
| *A61K 31/50* | (2006.01) |
| *A01N 43/60* | (2006.01) |
| *A61K 31/495* | (2006.01) |
| *A61K 31/497* | (2006.01) |
| *A01N 43/56* | (2006.01) |

(52) U.S. Cl. ............ 514/210.01; 514/210.16; 514/210.19; 514/210.2; 514/210.21; 514/247; 514/248; 514/249; 514/250; 514/252.1; 514/403; 514/405; 514/406; 514/407

(58) Field of Classification Search ............ 424/489; 514/210.01, 210.16, 210.19, 210.2, 210.21, 514/247, 248, 249, 250, 252.1, 403, 405, 514/406, 407

See application file for complete search history.

(56) References Cited

U.S. PATENT DOCUMENTS

| | | | |
|---|---|---|---|
| 2,750,393 | A | 6/1956 | Elpern |
| 2,967,194 | A | 1/1961 | Hauptschein |
| 3,917,625 | A | 11/1975 | Lee et al. |
| 3,950,351 | A | 4/1976 | Rossignol et al. |
| 4,009,174 | A | 2/1977 | Cluzan et al. |
| 4,105,785 | A | 8/1978 | Mauvernay et al. |
| 4,146,631 | A | 3/1979 | Ford et al. |
| 4,434,170 | A | 2/1984 | Dostert et al. |
| 4,474,792 | A | 10/1984 | Erickson |
| 4,634,783 | A | 1/1987 | Fujii et al. |
| 4,966,891 | A | 10/1990 | Fujiu et al. |
| 5,258,407 | A | 11/1993 | Washburn et al. |
| 5,273,986 | A | 12/1993 | Holland et al. |
| 5,399,702 | A | 3/1995 | Holland et al. |
| 5,466,715 | A | 11/1995 | Washburn et al. |
| 5,510,478 | A | 4/1996 | Sabb |
| 5,661,153 | A | 8/1997 | Isobe et al. |
| 5,672,750 | A | 9/1997 | Perry |
| 5,712,270 | A | 1/1998 | Sabb |
| 5,849,735 | A | 12/1998 | Albright et al. |
| 6,110,945 | A | 8/2000 | Head et al. |
| 6,197,798 | B1 | 3/2001 | Fink et al. |
| 6,200,995 | B1 | 3/2001 | De la Brouse-Elwood et al. |
| 6,207,693 | B1 | 3/2001 | Setoi et al. |
| 6,214,878 | B1 | 4/2001 | Bernardon et al. |
| 6,242,474 | B1 | 6/2001 | Yamasaki et al. |
| 6,255,335 | B1 | 7/2001 | Himmler et al. |
| 6,316,482 | B1 | 11/2001 | Setoi et al. |
| 6,320,050 | B1 | 11/2001 | Bizzarro et al. |
| 6,348,474 | B1 | 2/2002 | Kayakiri et al. |
| 6,369,229 | B1 | 4/2002 | Head et al. |
| 6,376,515 | B2 | 4/2002 | Zhu et al. |
| 6,388,071 | B2 | 5/2002 | Mahaney |
| 6,448,399 | B1 | 9/2002 | Corbett et al. |
| 6,486,349 | B1 | 11/2002 | Flitter et al. |
| 6,528,543 | B1 | 3/2003 | Haynes et al. |
| 6,545,155 | B2 | 4/2003 | Corbett et al. |
| 6,610,846 | B1 | 8/2003 | Bizzarro et al. |
| 6,613,942 | B1 | 9/2003 | Ling et al. |
| 7,132,546 | B2 | 11/2006 | Kato et al. |
| 7,199,140 | B2 | 4/2007 | Hayter et al. |
| 7,230,108 | B2 | 6/2007 | Hargreaves et al. |
| 2001/0027200 | A1 | 10/2001 | De la Brouse-Elwood et al. |
| 2002/0002183 | A1 | 1/2002 | Zhu et al. |
| 2002/0095044 | A1 | 7/2002 | Jagtap et al. |
| 2003/0162690 | A1 | 8/2003 | Zhu et al. |
| 2004/0014968 | A1 | 1/2004 | Bizzarro et al. |
| 2004/0077555 | A1 | 4/2004 | Ishihara et al. |
| 2005/0080106 | A1 | 4/2005 | Boyd et al. |
| 2005/0148605 | A1 | 7/2005 | Grotzfeld et al. |

(Continued)

FOREIGN PATENT DOCUMENTS

CA        2605738        11/2006

(Continued)

OTHER PUBLICATIONS

Boucherle et al. "Recherches dans la serie des cetones polyphenoliques IV. Thiazoles" Chimica Therapeutica. 3(5):360-363 (1968) (Translation enclosed).

(Continued)

*Primary Examiner*—Yong S Chong
(74) *Attorney, Agent, or Firm*—Morgan, Lewis & Bockius LLP

(57) ABSTRACT

A novel crystalline form of 3-{[5-(azetidin-1-ylcarbonyl)pyrazin-2-yl]oxy}-5-[(1-methylethyl)oxy]-N-1H-pyrazol-3-ylbenzamide is described in the specification. This compound is a glucokinase (GLK or GK) activator and useful as a pharmaceutical agent in the treatment or prevention of a disease or medical condition mediated through GLK, leading to a decreased glucose threshold for insulin secretion. Processes for the manufacture of the crystalline form, pharmaceutical compositions comprising the crystalline form and the use of the crystalline form in medical treatment are also described.

9 Claims, 2 Drawing Sheets

U.S. PATENT DOCUMENTS

| | | |
|---|---|---|
| 2005/0165074 A1 | 7/2005 | Grotzfeld et al. |
| 2005/0171171 A1 | 8/2005 | Mehta et al. |
| 2005/0171172 A1 | 8/2005 | Lai et al. |
| 2005/0261315 A1 | 11/2005 | Mehta et al. |
| 2006/0004010 A1 | 1/2006 | Habashita et al. |
| 2006/0167053 A1 | 7/2006 | Iino et al. |
| 2006/0258728 A1 | 11/2006 | Tani et al. |
| 2007/0078168 A1 | 4/2007 | Caulkett |

FOREIGN PATENT DOCUMENTS

| | | |
|---|---|---|
| CS | 173097 | 6/1978 |
| EP | 0316704 | 5/1989 |
| EP | 0353452 | 2/1990 |
| EP | 0219436 | 12/1993 |
| EP | 0619116 | 10/1994 |
| EP | 1048659 | 11/2000 |
| EP | 1132381 | 9/2001 |
| EP | 0620216 | 1/2003 |
| EP | 1336607 | 8/2003 |
| EP | 1357116 | 10/2003 |
| EP | 1400540 | 3/2004 |
| EP | 1496052 | 1/2005 |
| EP | 1600442 | 11/2005 |
| EP | 1702919 | 9/2006 |
| FR | 1526074 | 5/1968 |
| FR | 2088019 | 1/1972 |
| GB | 1352415 | 5/1974 |
| GB | 1561350 | 2/1980 |
| GB | 1588242 | 4/1981 |
| GB | 2216517 | 10/1989 |
| GB | 2331748 | 6/1999 |
| GB | 22385328 | 8/2003 |
| JP | 50105559 | 8/1975 |
| JP | 57021320 | 2/1982 |
| JP | 57075962 | 5/1982 |
| JP | 58069812 | 4/1983 |
| JP | 61205937 | 9/1986 |
| JP | 62158252 | 7/1987 |
| JP | 04300832 | 10/1992 |
| JP | 04300874 | 10/1992 |
| JP | 06027025 | 2/1994 |
| JP | 08143565 | 6/1996 |
| JP | 08173525 | 7/1996 |
| JP | 08301760 | 11/1996 |
| JP | 09040557 | 2/1997 |
| JP | 09202786 | 8/1997 |
| JP | 10101671 | 4/1998 |
| JP | 10101672 | 4/1998 |
| JP | 10212271 | 8/1998 |
| JP | 11029480 | 2/1999 |
| JP | 11171848 | 6/1999 |
| JP | 11222435 | 8/1999 |
| JP | 111292879 | 10/1999 |
| JP | 2000086657 | 3/2000 |
| WO | WO 91/09017 | 6/1991 |
| WO | WO 94/04525 | 3/1994 |
| WO | WO 94/12461 | 6/1994 |
| WO | WO 95/20578 | 8/1995 |
| WO | WO 95/35298 | 12/1995 |
| WO | WO 96/11902 | 4/1996 |
| WO | WO 96/19455 | 6/1996 |
| WO | WO 96/22282 | 7/1996 |
| WO | WO 96/22293 | 7/1996 |
| WO | WO 96/22294 | 7/1996 |
| WO | WO 96/22295 | 7/1996 |
| WO | WO 96/36619 | 11/1996 |
| WO | WO 96/41795 | 12/1996 |
| WO | WO 97/24355 | 7/1997 |
| WO | WO 97/36480 | 10/1997 |
| WO | WO 97/46560 | 12/1997 |
| WO | WO 97/49707 | 12/1997 |
| WO | WO 97/49708 | 12/1997 |
| WO | WO 98/24771 | 6/1998 |
| WO | WO 98/34632 | 8/1998 |
| WO | WO 98/45242 | 10/1998 |
| WO | WO 99/00359 | 1/1999 |
| WO | WO 99/00372 | 1/1999 |
| WO | WO 99/17777 | 4/1999 |
| WO | WO 99/20611 | 4/1999 |
| WO | WO 99/24415 | 5/1999 |
| WO | WO 99/26944 | 6/1999 |
| WO | WO 99/32477 | 7/1999 |
| WO | WO 99/38845 | 8/1999 |
| WO | WO 99/54301 | 10/1999 |
| WO | WO 99/62901 | 12/1999 |
| WO | WO 00/02850 | 1/2000 |
| WO | WO 00/26202 | 5/2000 |
| WO | WO 00/39118 | 7/2000 |
| WO | WO 00/46203 | 8/2000 |
| WO | WO 00/58293 | 10/2000 |
| WO | WO 01/00579 | 1/2001 |
| WO | WO 01/12621 | 2/2001 |
| WO | WO 01/16097 | 3/2001 |
| WO | WO 01/19788 | 3/2001 |
| WO | WO 01/20327 | 3/2001 |
| WO | WO 01/26652 | 4/2001 |
| WO | WO 01/32639 | 5/2001 |
| WO | WO 01/44216 | 6/2001 |
| WO | WO 01/64642 | 9/2001 |
| WO | WO 01/64643 | 9/2001 |
| WO | WO 01/74791 | 10/2001 |
| WO | WO 01/83465 | 11/2001 |
| WO | WO 01/83478 | 11/2001 |
| WO | WO 01/85706 | 11/2001 |
| WO | WO 01/85707 | 11/2001 |
| WO | WO 02/00633 | 1/2002 |
| WO | WO 02/08209 | 1/2002 |
| WO | WO 02/14312 | 2/2002 |
| WO | WO 02/24682 | 3/2002 |
| WO | WO 02/26718 | 4/2002 |
| WO | WO 02/26731 | 4/2002 |
| WO | WO 02/28835 | 4/2002 |
| WO | WO 02/42270 | 5/2002 |
| WO | WO 02/46173 | 6/2002 |
| WO | WO 02/48106 | 6/2002 |
| WO | WO 02/051831 | 7/2002 |
| WO | WO 02/064545 | 8/2002 |
| WO | WO 02/079145 | 10/2002 |
| WO | WO 03/000262 | 1/2003 |
| WO | WO 03/000267 | 1/2003 |
| WO | WO 03/015518 | 2/2003 |
| WO | WO 03/015774 | 2/2003 |
| WO | WO 03/022856 | 3/2003 |
| WO | WO 03/024222 | 3/2003 |
| WO | WO 03/026652 | 4/2003 |
| WO | WO 03/028641 | 4/2003 |
| WO | WO 03/047626 | 6/2003 |
| WO | WO 03/048152 | 6/2003 |
| WO | WO 03/051366 | 6/2003 |
| WO | WO 03/055482 | 7/2003 |
| WO | WO 03/066613 | 8/2003 |
| WO | WO 03/080585 | 10/2003 |
| WO | WO 03/082838 | 10/2003 |
| WO | WO 03/095438 | 11/2003 |
| WO | WO 03/097824 | 11/2003 |
| WO | WO 2004/002481 | 1/2004 |
| WO | WO 2004/022536 | 3/2004 |
| WO | WO 2004/031179 | 4/2004 |
| WO | WO 2004/045614 | 6/2004 |
| WO | WO 2004/046139 | 6/2004 |
| WO | WO 2004/050645 | 6/2004 |
| WO | WO 2004/052869 | 6/2004 |
| WO | WO 2004/063179 | 7/2004 |

| WO | WO 2004/063194 | 7/2004 |
| WO | WO 2004/072031 | 8/2004 |
| WO | WO 2004/072066 | 8/2004 |
| WO | WO 2004/076420 | 9/2004 |
| WO | WO 2004/081001 | 9/2004 |
| WO | WO 2004/085385 | 10/2004 |
| WO | WO 2004/085406 | 10/2004 |
| WO | WO 2004/110350 | 12/2004 |
| WO | WO 2004/110375 | 12/2004 |
| WO | WO 2005/044801 | 5/2005 |
| WO | WO 2005/048953 | 6/2005 |
| WO | WO 2005/049019 | 6/2005 |
| WO | WO 2005/054200 | 6/2005 |
| WO | WO 2005/054233 | 6/2005 |
| WO | WO 2005/056530 | 6/2005 |
| WO | WO 2005/063738 | 7/2005 |
| WO | WO 2005/066145 | 7/2005 |
| WO | WO 2005/080359 | 9/2005 |
| WO | WO 2005/080360 | 9/2005 |
| WO | WO 2005/090332 | 9/2005 |
| WO | WO 2005/095417 | 10/2005 |
| WO | WO 2005/095418 | 10/2005 |
| WO | WO 2005/103021 | 11/2005 |
| WO | WO 2005/121110 | 12/2005 |
| WO | WO 2005/123132 | 12/2005 |
| WO | WO 2006/016174 | 2/2006 |
| WO | WO 2006/016178 | 2/2006 |
| WO | WO 2006/016194 | 2/2006 |
| WO | WO 2006/040527 | 4/2006 |
| WO | WO 2006/040528 | 4/2006 |
| WO | WO 2006/040529 | 4/2006 |
| WO | WO 2006/066613 | 6/2006 |
| WO | WO 2006/114180 | 11/2006 |
| WO | WO 2006/125958 | 11/2006 |
| WO | WO 2006/125972 | 11/2006 |
| WO | WO 2007/007040 | 1/2007 |
| WO | WO 2007/007041 | 1/2007 |
| WO | WO 2007/007042 | 1/2007 |
| WO | WO 2007/017649 | 2/2007 |
| WO | WO 2007/028135 | 3/2007 |
| WO | WO 2007/031739 | 3/2007 |
| WO | WO 2007/053657 | 5/2007 |
| WO | WO 2007/060448 | 5/2007 |
| WO | WO 2008/050101 | 5/2008 |
| WO | WO 2008/050117 | 5/2008 |
| WO | WO 2008/075073 | 6/2008 |

OTHER PUBLICATIONS

Bowden et al. "Structure-activity relations. Part 10. Metal-ion-complexation studies of a series of substituted benzamidotetrazoles" J. Chem. Research (Synopses) 11:304 (1991).
Bowden et al. "Structure-activity relations. Part 13. Inhibitors of cyclic nucleotide phosphodiesterase and anaphylaxis. Inhibition by a series of substituted benzamidotetrazoles" J. Chem. Research (Synopses) 6:206 (1992).
Brenner et al. "Imino-bridged heterocycles. VII. (1) N-aminobenzocycloheptapyridinimines" J. Heterocyclic Chem. 23:1331-1332 (1986).
Brocklehurst et al. "Stimulation of hepatocyte glucose metabolism by novel small molecule glucokinase activators" Diabetes 53:535-541 (2004).
Caro et al. "Liver glucokinase: Decreased activity in patients with type II diabetes" Horm. Metab. Res. 27(1):19-22 (1995).
Carroll et al. "The in vitro characterisation of a novel Glucokinase activator" Stress, Signalling and Control, Biochemical Society Meeting 679, University of Essex, UK (Jul. 2-4, 2003).
Caulfield et al. "The first potent and selective inhibitors of the glycine transporter type 2" J. Med. Chem. 44(17):2679-2682 (2001).
Cavier et al. "Recherches sur les derives nitres d'interet biologique. XVI. Relations entre structures et activites protozoocides, anthelminthiques et molluscicides dans la serie du benzamido-2 nitro-5 thiazole" European Journal of Medicinal Chemistry, Chimica Therapeutica 13(6): 539-543 (1978) (Translation enclosed).
Chemical Abstracts Service, Columbus, Ohio, US: CAS Registry No. 438028-05-8 (Nov. 15, 2001); CAS Registry No. 438024-90-9 (Nov. 15, 2001), [XP002272448].
Chemical Abstracts Service, Columbus, Ohio, US: CAS Registry No. 445284-93-5 (Jul. 9, 2002); CAS Registry No. 445250-52-2 (Jul. 9, 2002); CAS Registry No. 445030-98-8 (Jul. 9, 2002); CAS Registry No. 445017-74-3 (Jul. 9, 2002); CAS Registry No. 444935-78-8 (Jul. 9, 2002); CAS Registry No. 444923-81-3 (Jul. 9, 2002); CAS Registry No. 438222-80-1 (Jul. 9, 2002); CAS Registry No. 438221-01-3 (Jul. 9, 2002); CAS Registry No. 354550-59-7 (Jul. 9, 2002); CAS Registry No. 438537-80-5 (Jul. 9, 2002); CAS Registry No. 353770-14-6 (9 Jul 2002); CAS Registry No. 352690-95-0 (Jul. 9, 2002); CAS Registry No. 353478-21-4 (Jul. 9, 2002); CAS Registry No. 353477-20-0 (Jul. 9, 2002): CAS Registry No. 353474-36-9 (Jul. 9, 2002); CAS Registry No. 362473-72-1 (Jul. 9, 2002); CAS Registry No. 303140-37-6 (Jul. 9, 2002); [XP002272449].
Chemical Abstracts Service, Columbus, Ohio, US: CAS Registry No. 354767-51-4 (Sep. 5, 2001).
Chemical Abstracts Service, Columbus, Ohio, US: CAS Registry No. 354767-66-1 (Sep. 5, 2001).
Christesen et al. "The second activating glucokinase mutation (A456V): Implications for glucose homeostasis and diabetes therapy" Diabetes 51(4):1240-1246 (2002).
Ciaceri et al. "Analgesic, antipyretic and anti-inflammatory action of some new acids of the phenylethylenethiazole series" Minerva Medica 63(42):2409-2413 (1972).
Coburn et al. "Mesoionic purinone analogs IV: Synthesis and in vitro antibacterial properties of mesoionic thiazolo(3,2-α)pyrimidin-5,7-diones and mesoionic 1,3,4-thiadizolo(3,2-α)pyrimidin-5,7-diones" J. Pharm. Sciences. 62(11):1785-1789 (1973).
Coghlan "Small molecule Glucokinase Activators (GKAs) as novel anti-diabetic agents" CIDEM seminar (May 2005).
Coghlan "Small molecule Glucokinase Activators (GKAs) as novel anti-diabetic agents" Society for Medicines Research Seminar (Jun. 2004).
Coope et al. "Predictive blood glucose lowering efficacy by Glucokinase activators in high fat fed female Zucker rats" British Journal of Pharmacology 149(3):328-335 (2006).
Corbett "Glucokinase activators: Discovery of novel, orally active glucose lowering agents" Abstract, Cambridge Healthtech Institute's Eleventh Annual Molecular Medicine Tri-Conference, Moscone West Convention Center, San Francisco, CA (Mar. 24-26, 2004).
Corbett "Glucokinase activators: Discovery of novel, orally active glucose lowering agents" Presentation Slides, Cambridge Healthtech Institute's Eleventh Annual Molecular Medicine Tri-Conference, Moscone West Convention Center, San Francisco, CA (Mar. 24-26, 2004).
Cushman et al. "Synthesis and evaluation of new protein-tyrosine kinase inhibitors. Part 1. Pyridine-containing stilbenes and amides" Bioorganic & Medicinal Chemistry Letters 1(4):211-214 (1991).
De Paulis et al. "Potential antipsychotic agents. 6. Synthesis and antidopaminergic properties of substituted N-(1-benzyl-4-piperidinyl)salicylamides and related compounds. QSAR based design of more active members" Eur. J. Med. Chem. 25:507-517 (1990).
DeFronzo et al. "The triumvirate: β-cell, muscle, liver. A collusion responsible for NIDDM" Diabetes 37:667-687 (1988).
DeJohn et al. "Functionalization of Substituted 2(1H)- and 4(1H)-Pyridones. III. The preparation of substituted 6-vinyl-1,2-dihydro-2-oxo—and 1,4-dihydro-4-oxo-3-pyridinecarboxylic acids through the chemistry of pyridone dianions" J. Heterocyclic Chem. 20(5):1295-1302 (1983).
Desai et al. "Phenotypic correction of diabetic mice by adenovirus-mediated glucokinase expression" Diabetes 50:2287-2295 (2001).
Edmont et al. "Synthesis and evaluation of quinoline carboxyguanidines as antidiabetic agents" Bioorg. Med. Chem. Lett. 10(16):1831-1834 (2000).
Elpern et al. "Iodinated Benzamidotetrazoles" J. Org. Chem. 22: 1686 (1957).
Ferre et al. "Correction of diabetic alterations by glucokinase" PNAS USA 93(14):7225-7230 (1996).

Ford et al. "Synthesis and quantitative structure-activity relationships of antiallergic 2-hydroxy-N-1H-tetrazol-5-ylbenzamides and N-(2-hydroxyphenyl)-1H-tetrazole-5-carboxamides" J. Med. Chem. 29(4):538-549 (1986).

Froguel et al. "Familial hyperglycemia due to mutations in glucokinase—Definition of a subtype of diabetes mellitus" New Engl. J. Med. 328:697-702 (1993).

Fujimoto et al. "Administration of D-glucosamine into the third cerebroventricle induced feeding accompanied by hyperglycemia in rats" Life Sciences 37(26):2475-2482 (1985).

Gill et al. "Stimulation of insulin release by a small molecule glucokinase activator" EASD Islet Study Group, Abstract (Nov. 2005).

Gill et al. "Stimulation of Insulin Release in MIN6 Cells and Isolated Rodent Islets by a Small Molecule Glucokinase Activator (GKA50)" Poster presented at 42nd EASD Meeting Copenhagen (2006) and Diabetologia vol. 49 (Supplement 1) 0501 (2006).

Gill et al. "Upregulation of key β-cell genes and improvement of function in rodent islets following chronic in vitro treatment with a glucokinase activator" Poster presented at 43rd EASD Meeting, Amsterdam (Sep. 17-21, 2007) and Diabetologia vol. 50 (Supplement 1) S218 (2007).

Glaser et al. "Familial hyperinsulinism caused by an activating glucokinase mutation" The New England Journal of Medicine 338(4):226-230 (1998).

Gorman et al. "Effect of high-fat diet on glucose homeostasis and gene expression in Glucokinase (GK) heterozygous knock-outs" Abstract Number: 0108-OR, 67th Annual Scientific Sessions, American Diabetes Association, Chicago, IL (Jun. 22-26, 2007).

Grimsby "Glucokinase activators: Potential treatment for type 2 diabetes" Roche, SMi Diabetes, London, UK (Oct. 28-29, 2002).

Grimsby et al. "Allosteric activators of glucokinase: Potential role in diabetes therapy" Science 301(5631):370-373 (2003).

Guertin et al. "Small molecule glucokinase activators as glucose lowering agents: A new paradigm for diabetes therapy" Current Medicinal Chemistry 13(15):1839-1843 (2006).

Hashimoto et al. "Evaluation of differentiation-inducing activity of retinoids on human leukemia cell lines HL-60 and NB4" Biol. Pharm. Bull. 19(10):1322-1328 (1996).

Hirst et al. "Molecular recognition of phosphate esters: A balance of hydrogen bonding and proton transfer interactions" Israel Journal of Chemistry 32:105-111 (1992).

Horsak et al. "Method of evaluation of the phase diagram of a system with formation of a compound" Chem. Zvesti. 36(3):311-320 (1982).

Isomura et al. "Z-type deposition of a polymerizable amphiphile to fabricate an immobilized LB film showing strong second harmonic generation" Thin Solid Films 244:939-942 (1994).

Johnson et al. "Glucose-dependent modulation of insulin secretion and intracellular calcium ions by GKA50—A glucokinase activator" Abstract No. 0592-P, 67th Annual Scientific Sessions, American Diabetes Association, Chicago, IL (Jun. 22-26, 2007).

Julia et al. "Synthesis of a 2,3,4,4a,5,6-hexahydrobenzo[f]quinoline system by "aryne substitution"" Bull Chem Soc France 11:4463-4467 (1968) (Translation enclosed).

Kamata et al. "Pyroelectricity of noncentrosymmetric Langmuir-Blodgett films of phenylpyrazine derivatives" Japan J. Appl. Phys. 33(2):1074-1078 (1994).

Kar "Cinchophen analogues as potential CNS agents" J Pharm Sci. 72(9):1082-1084 (1983).

Knoppova et al. "Synthesis and properties of 5-styryl-2-furancarboxlic acids" Collection Czechoslovak Chem. Commun. 46:2716-2728 (1981).

Konig et al. "Binding of heptanedioic acid to threefold pyridine arylamide receptor. Enhancement of the stability of supramolecular solution structures by multiple binging sites" J. Org. Chem. 60(13):4291-4293 (1995).

Kunishima et al. "4-(4,6-Dimethoxy-1,3,5-triazin-2-yl)-4-methylmorpholinium chloride: An efficient condensing agent leading to the formation of amides and esters" Tetrahedron 55:13159-13170 (1999).

Kurata et al. "D-Glucose suppression of eating after intra-third ventricle infusion in rat" Physiology & Behavior 37:615-620 (1986).

Kurata et al. "Structural evaluation of glucose analogues on feeding elicitation in rat" Metabolism 38(1):46-51 (1989).

Lai et al. "Formation of columnar arrangements in copper(ii) complexes of 2-phenylazomethinopyridine derivatives" J. Materials Chemistry 8(11):2379-2383 (1998).

Leighton et al. "Improved glycemic control after sub-acute administration of a Glucokinase activator to male zucker (fa/fa) rats" Abstract No. 0377-OR, 67th Annual Scientific Sessions, American Diabetes Association, Chicago, IL (Jun. 22-26, 2007).

Leighton et al. "Small molecule glucokinase activators as novel antidiabetic agents" Biochemical Society Transactions 33(Part 2):371-374 (2005).

Levin "Glucosensing neurons do more than just sense glucose" International Journal of Obesity 25(Suppl 5): S68-S72 (2001).

Levin et al. "Brain glucose sensing and body energy homeostasis: role in obesity and diabetes" Am. J. Physiol. 276(5 Pt2):R1223-R1231 (1999).

Levin et al. "Differential effects of diet and obesity on high and low affinity sulfonylurea binding sites in the rat brain" Brain Research 739(1-2):293-300 (1996).

Caira "Crystalline polymorphism of organic compounds" Topics in Current Chemistry 198:163-208 (1998).

Eycken et al., Synthesis of (E)-5-(2-arylvinyl)-2-(hetero)arylpyridines, (E)-2-(2-arylvinyl)-5-methoxycarbonylpyridines and (E,E)-2,5-bis(2-arylvinyl)pyridines as polarity and pH probes, 2002, J. Chem. Soc., Perkin. Trans. 2, p. 929.

Robertson et al. "Structure-activity relationships of arylimidazopyridine cardiotonics: discovery and inotropic activity of 2-[2-methoxy-4-(methylsulfinyl)phenyl]-1H-imidazo[4,5-c]pyridine" Journal of Medicinal Chemistry 28:717-727 (1985).

West, Anthony R., "Solid State Chemistry and its Applications" Wiley, New York, pp. 358 and 365 (1988).

Wolff, Manfred E. "Burger's Medicinal Chemistry", 5th Edition, Part I, John Wiley & Sons, pp. 975-977 (1995).

Coghlan et al., "Glucokinase activators in diabetes management" Expert Opin. Investig. Drugs 17(2):145-167 (2008).

Leighton, "Pre-clinical disease models—challenges and success stories"44th Drug Information Association Annual Meeting, Boston, MA, US (2008).

Lith, "Evaluation of the effects on whole body glucose metabolism after single doses of X2000—A glucose lowering agent" Poster presentation, Master thesis in Pharmaceutical Bioscience, Goteborgs University (2008).

Ralph et al. "Glucose Modulation of Glucokinase Activation by Small Molecules" Biochemistry 47(17):5028-5036 (2008).

Sarabu et al., "Glucokinase activators as new type 2 diabetes therapeutic agents" Expert Opinion on Therapeutic Patents 18(7):759-768 (2008).

Shorvon, "Pyrrolidone derivatives" Lancet 358(9296):1885-1892 (2001).

Alvarez et al. "Evidence that glucokinase regulatory protein is expressed and interacts with glucokinase in rat brain" J. Neurochem. 80(1):45-53 (2002).

Alvarez et al. "Expression of the glucagon-like peptide-1 receptor gene in rat brain" J. Neurochem. 66(3):920-927 (1996).

Anderson et al "Pyridopyrimidines. 6. Nucleophilic substitutions in the pyrido[2,3-d]pyrimidine series" J. Org. Chem. 42(6):993-996 (1977).

Ando et al. "Fluoride salts on alumina as reagents for alkylation of phenols and alcohols" Bull. Chem. Soc. Jpn. 55(8):2504-2507 (1982).

Atwell et al. "Potential antitumor agents. VI. Bisquaternary salts" J. Med. Chem. 11(2):295-300 (1968).

Baker et al. "Structure and synthesis of Pallescansin E utilising a modified Wadsworth-Emmons reaction" J. Chem. Soc., Perkin Trans. 1, 12:3087-3091 (1981).

Baker et al. "Synthesis of Pallescensin-E: Use of crown ether in the Wadsworth procedure for olefin formation" Tetrahedron Letters 22:161-162 (1981).

Balant et al. "Metabolic considerations in prodrug desing" Chapter twenty-three, Burger's Medicinal Chemistry and Drug Discovery, 5th Edition, vol. 1, NY: John Wiley & Sons, Inc. 949-982 (1995).

Beilstein Registry No. 6511458 (Apr. 18, 1994) [XP002272206].

Bell et al. "Glucokinase mutations, insulin secretion, and diabetes mellitus" Annu. Rev. Physiol. 58:171-186 (1996).

Beller et al. "Photochemical synthesis of benzo[f]quinolines" J Org Chem. 42(22):3514-3518 (1977).

Berl et al. "Induced fit selection of a barbiturate receptor from a dynamic structural and conformational/ configurational library" European J. Org. Chem. (11):3089-3094 (1999).

Berl et al. "Template-induced and molecular recognition directed hierarchical generation of supramolecular assemblies from molecular strands" Chem. Eur. J. 6(11):1938-1946 (2000).

Bonina et al. "Synthesis and pharmacologic activity of 2-arylethenylthiazol-4-acetic and 4-carboxylic acids" II Farmaco 40(11):875-884 (1985).

Levin et al. "In vivo and in vitro regulation of [3H]glyburide binding to brain sulfonylurea receptors in obesity-prone and resistant rats by glucose" Brain Research 776(1-2):146-153 (1997).

Levin et al. "Reduced glucose-induced neuronal activation in the hypothalamus of diet-induced obese rats" Brain Research 808(2):317-319 (1998).

Levkoev et al. "Research on cyanide dyes 11. 7,7'-Dimethylthiacarbocyanines" Zhurnal Obshchei Khimii 27:3097-3107 (1957) (Translation enclosed).

Lynch et al. "Localization of glucokinase gene expression in the rat brain" Diabetes 49(5):693-700 (2000).

Mastafanova et al. "Features of the catalytic reduction of 4-(3-oxoquinuclidyl-2-methylene)-6-methoxyquinoline and its ethyleneketal" Khimiya Geterotsiklicheskikh Soedinenii (1):86-94 (1989) (Translation enclosed).

Mastafanova et al. "Synthesis and study of the antihypertensive activity of substituted N-acetylmercaptopropionyl-6-[2'-phenylethyl]pipecolinic acids" Khimiko Farmatsevticheskii Zhurnal 22(3)294-302 (1988).

Mastafanova et al. "Synthesis, Anti-Inflammatory and Analgesic Activity of 1,6-Disubstituted Pipecolic and 6-Substituted Picolinic Acids" Khimiko Farmatsevticheskii Zhurnal 22(4) 428-431 (1988).

Mazik et al. "Molecular recognition of carbohydrates by artificial receptors: systematic studies towards recognition motifs for carbohydrates" Chem. Eur. J. 7(3):664-670 (2001).

Mazik et al. "Molecular recognition of carbohydrates by artificial polypyridine and polypyrimidine receptors" Angewandte Chemie International Edition 39(3):551-554 (2000).

McKerrecher "Design and synthesis of novel glucokinase activators" 13th RSC-SCI Medicinal Chemistry Symposium, Churchill College, Cambridge (Sep. 4-7, 2005).

McKerrecher et al. "Design & synthesis of novel glucokinase activators as potential treatments for type 2 diabetes" 233rd ACS National Meeting, Chicago, IL (Mar. 25-29, 2007).

McKerrecher et al. "Design and synthesis of novel glucokinase activators as potential treatment for type 2 diabetes" Frontiers in Medicinal Chemistry, Frankfurt (Mar. 12-15, 2006).

McKerrecher et al. "Design of a potent, soluble glucokinase activator with excellent in vivo efficacy" Bioorg. Med. Chem. Lett. 16(10):2705-2709 (May 15, 2006) Epub Feb. 28, 2006.

McKerrecher et al. "Discovery, synthesis and biological evaluation of novel glucokinase activators" Bioorg Med Chem Lett. 15(8):2103-2106 (2005).

McKerrecher et al. "Identification of orally bioavailable small molecule activators of glucokinase" Abstract, 12th SCI-RSC Medicinal Chemistry Symposium, Cambridge, UK, Sep. 7-10, 2003 (poster 21) and 227th American Chemical Society National Meeting and Exposition, San Francisco, California, Mar. 28-Apr.1, 2004 (paper 341).

McKerrecher et al. "Identification of orally bioavailable small molecule activators of glucokinase" Abstract, Anglo-Swedish Medicinal Chemistry Meeting (Mar. 2005).

Meijer et al "Chiral amplification in supramolecular stacks" Polymer Preprints 41(1):902-903 (2000).

Mobbs et al. "Brain glucose-sensing mechanisms: ubiquitous silencing by aglycemia vs. hypothalamic neuroendocrine responses" Am. J. Physiol. Endocrinol. Metab. 281(4):E649-E654 (2001).

Moore et al. "Acute fructose administration improves oral glucose tolerance in adults with type 2 diabetes" Diabetes Care 24(11):1882-1887 (2001).

Motesharei et al. "Molecular recognition in membrane mimics: A fluorescence probe" J. Am. Chem. Soc. 116(16):7413-7414 (1994).

Motesharei et al. "Molecular recognition on functionalized self-assembled monolayers of alkanethiols on gold" J. Am. Chem. Soc. 120(29): 7328-7336 (1998).

Palmans "Extended-core discotic liquid crystals based on the intramolecular H-bonding in N-acylated 2,2'-bipyridine3,3'-diamine moieties" Chem. Eur. J. 3(2):300-307 (1997).

Plieninger et al. "Synthesis of 7,8-dihydro-5,6-benzoquinoline-(3)-carboxylic acid" Chemische Berichte 87:882-887 (1954) (Translation enclosed).

Printz et al. "Mammalian glucokinase" Annu. Rev. Nutr. 13:463-496 (1993).

Prousek et al. "Preparation and electron transfer-induced cis-trans isomerization reactions of 1-(5-nitro-2-furyl)-, 1-(5-nitro-2-thienyl)-, and 1-(4-nitrophenyl)-2-R ethylenes" Collect. Czech. Chem. Commun. 54:1675-1682 (1989).

Qian-Cutrone et al. "Glucolipsin A and B, two new glucokinase activators produced by *Streptomyces purpurogeniscleroticus* and *Nocardia vaccinii*" Journal of Antibiotics (Tokyo), 52(3):245-255 (1999).

Rivalle et al. "2,3 Disubstituted furans and pyrroles—XVIII: Synthesis annd rearrangement of 4H-dihydro-9,10 benzo[4,5]cyclohepta[1,2-b]furannones-4" Tetrahedron 32(7):829-834 (1976).

Rogers et al. "Mesoionic purinone analogues as inhibitors of cyclic-AMP phosphodiesterase: a comparison of several ring systems" J. Med. Chem. 24(11):1284-1287 (1981).

Roncero et al. "Functional glucokinase isoforms are expressed in rat brain" J. Neurochem. 74(5):1848-1857 (2000).

Rowe et al. "Potassium channel dysfunction in hypothalamic glucose-receptive neurones of obese Zucker rats" Journal of Physiology 497.2:365-377 (1996).

Schuit et al. "Glucose sensing in pancreatic β-Cells. A model for the study of other glucose-regulated cells in gut, pancreas, and hypothalamus" Diabetes 50:1-11 (2001).

Sekera et al. "No. 69.—Recherches sur les anesthesiques locaux (XI memoire) Synthese de quelques nouveaux β-alcoxyethoxycarbanilates et β-alcoxyethoxycinchonamides amines" Soc. Chim 5th Series, Memoires 401-404 (1959). (Translation enclosed).

Seoane et al. "Glucokinase overexpression restores glucose utilization and storage in cultured hepatocytes from male Zucker diabetic fatty rats" J Biol Chem. 274(45):31833-31838 (1999).

Shiota et al. "Glucokinase gene locus transgenic mice are resistant to the development of obesity-induced type 2 diabetes" Diabetes 50(3):622-629 (2001).

Spanswick et al. "Insulin activates ATP-sensitive K+ channels in hypothalamic neurons of lean, but not obese rats" Nature Neuroscience 3(8):757-758 (2000).

Spanswick et al. "Leptin inhibits hypothalamic neurons by activation of ATP-sensitive potassium channels" Nature 390(6659):521-525 (1997).

Stout et al. "Synthesis and antiarrhythmic and parasympatholytic properties of substituted phenols. 3. Modifications to the linkage region (region 3)" J. Med. Chem. 28(3):295-298 (1985).

Suhua et al. "Synthesis and biological activity of tyrosine protein kinase inhibitors" Acta Pharmaceutica Sinica 32(7): 515-523 (1997).

Tecilla et al. "Hydrogen-bonding self-assembly of multichromophore structures" J. Am. Chem. Soc. 112:9408-9410 (1990).

Tecilla et al. "Synthetic hydrogen bonding receptors as models of transacylase enzymes" Tetrahedron 51(2):435-448 (1995).

Tecilla et al. "Transition-state stabilization and molecular recognition: acceleration of phosphoryl-transfer reactions by an artificial receptor" J. Am. Chem. Soc. 112:9586-9590 (1990).

Tornetta et al. "Arylvinylthiazole derivatives with anti-inflammatory, analgesic and anti-pyretic activity" Bollettino Delle Sedute Accad. Giovenia Sci. Nat. Catanica. Series 6, 11(9-10):89-95 (1973) (Translation enclosed).

Tucker et al. "Novel Inhibitors of prolyl 4-hydroxylase. 2. 5-amide substituted pyridine-2-carboxylic acids" J. Med. Chem. 3(5)5:804-807 (1992).

Van Gorp et al. "C3-symmetrical supramolecular architectures: fibers and organic gels from discotic trisamides and trisureas" J Am. Chem. Soc. 124(49):14759-14769 (2002).

Vanderstelt et al. "Synthesis and pharmacological properties of some derivatives of 5H-benzo[4,5]cyclohepta[1,2-b]pyridine and of 11H-benzo[5,6]cyclohepta[1,2-c] pyridine III" Arzneim. Forsch. 22(1):133-137 (1972).

Velho et al. "Impaired hepatic glycogen synthesis in glucokinase-deficient (MODY-2) subjects" J. Clin. Invest. 98(8):1755-1761 (1996).

Vertigan et al. "Impact of cell glycogen content on modulation of hepatocyte glucose metabolism by pharmacological agents" Diabetologia, 47 Supp 1, A 214, 589 (2004).

Williams et al. "Meeting the needs of type 2 diabetes patients" Highlights from the society for medicines research symposium type II diabetes: Mechanisms and emerging therapeutic targets, held Jun. 17, 2004, in London, United Kingdom, Drug News and Perspectives, 17(8) 1-4 (Oct. 2004).

Winzell et al. "Glucokinase Activation Reduces Glycemia and Improves Glucose Tolerance in Mice with High-fat Diet-induced Insulin Resistance" Abstract No. 1482-P, 67th Annual Scientific Sessions, American Diabetes Association, Chicago, IL (Jun. 22-26, 2007) and Diabetes vol. 56 (Supplement 1) 1482-P (2007).

Yakushijin et al. "Intramolecular ring formation of phenyl azide and furan" Heterocycles 12(8):1021-1026 (1979).

Yakushijin et al. "Intramolecular ring formation of phenyl azide and furan moieties" Chem. Pharm. Bull. 30(1):140-151 (1982).

Yang et al. "Hypothalamic glucose sensor: similarities to and differences from pancreatic beta-cell mechanisms" Diabetes 48(9):1763-1772 (1999).

Yoshina et al. "Studies of heterocyclic compounds. II. Synthesis of 2-furylvinyl-benzenes and studies of polarography" Yakugaku Zasshi 88(4):398-404 (1968).

Yoshina et al. "Studies of heterocyclic compounds. III. Synthesis of methyl 5-(2-phenylvinyl)2-furoate" Yakugaku Zasshi 88(4):405-409 (1968).

Yoshina et al. "Studies of heterocyclic compounds. IV. Ultraviolet spectra of 2(2-furyl)vinylbenzenes and 2-(2-furyl)vinylfurans" Yakugaku Zasshi 88(4):410-416 (1968).

Yoshina et al. "Studies of heterocyclic compounds. VI. 2-)Carbomethoxy-2-furyl)vinyl benzenes and their ultraviolet spectra" Yakugaku Zasshi 88(4):977-983 (1968).

Youssefyeh et al. "Development of high-affinity 5-HT3 receptor antagonists. 1. Initial structure-activity relationship of novel benzamides" J. Med. Chem. 35(5): 895-903 (1992).

Zhang et al. "Synthesis based on affinity separation (SAS): separation of products having barbituric acid tag from untagged compounds by using hydrogen bond interaction" Synlett 5:590-596 (2001).

Figure A: X-Ray Powder Diffraction Pattern of Form B
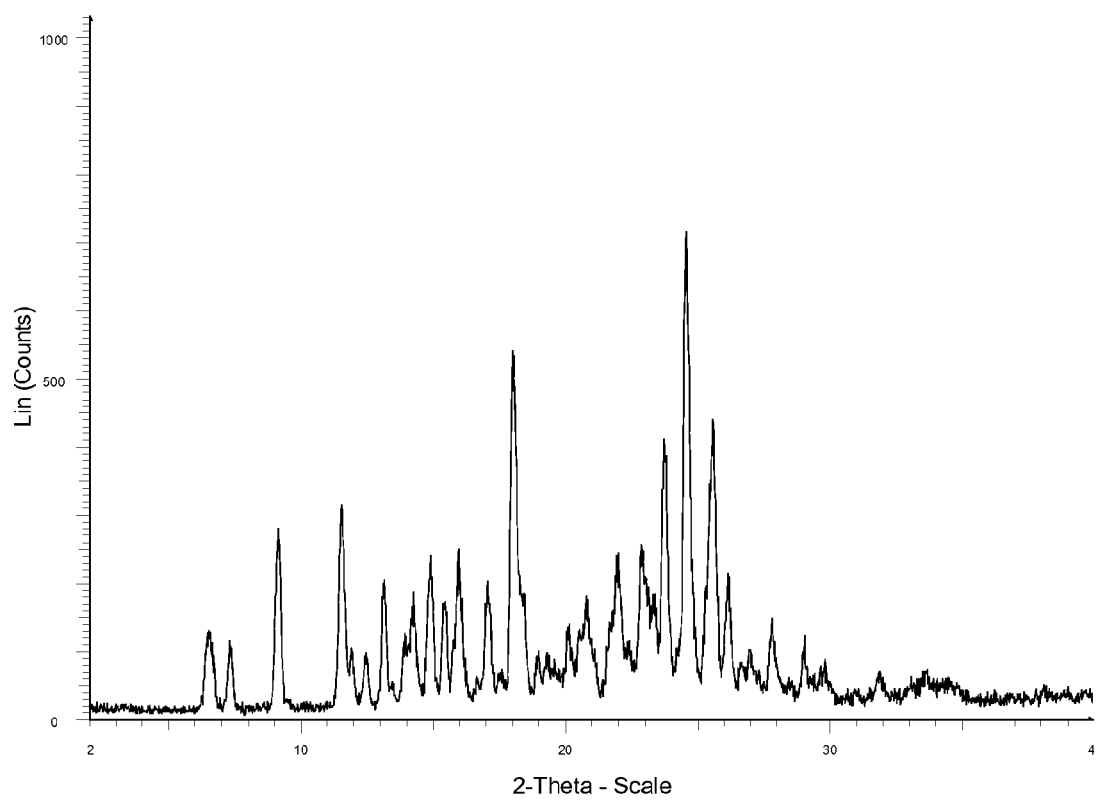

Figure B: DSC Thermogram of Form B
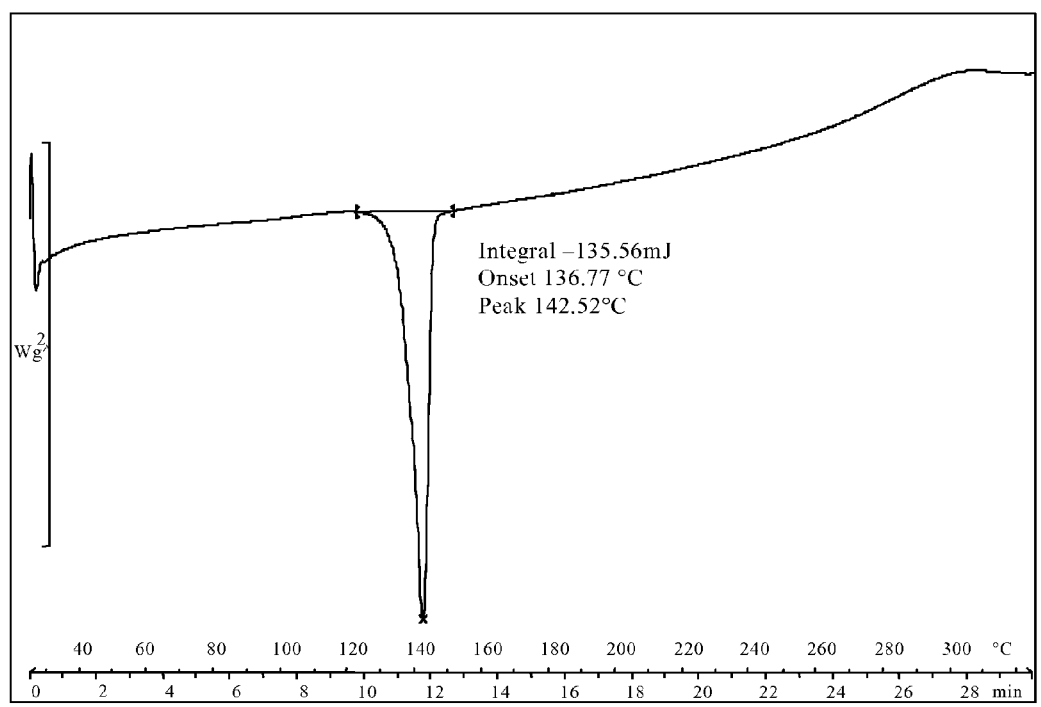

CRYSTALLINE COMPOUND

CROSS-REFERENCE TO RELATED APPLICATIONS

This application claims the benefit under 35 U.S.C. § 119 (e) of U.S. application Ser. No. 60/871,255 filed on Dec. 21, 2006.

FIELD OF INVENTION

The present invention relates to a novel crystalline chemical compound and more particularly to a novel crystalline form of 3-{[5-(azetidin-1-ylcarbonyl)pyrazin-2-yl]oxy}-5-[(1-methylethyl)oxy]-N-1H-pyrazol-3-ylbenzamide, hereinafter referred to as "the Agent", and illustrated in Formula (I) hereinafter, which compound is a glucokinase (GLK or GK) activator and useful as a pharmaceutical agent in the treatment or prevention of a disease or medical condition mediated through GLK, leading to a decreased glucose threshold for insulin secretion. The invention also relates to processes for the manufacture of the crystalline form, pharmaceutical compositions comprising the crystalline form and the use of the crystalline form in medical treatment.

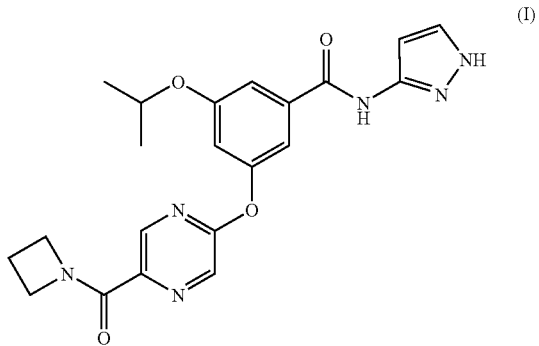

(I)

BACKGROUND OF THE INVENTION

International patent application PCT/GB2006/002471 (WO2007/007041) discloses the Agent in 2 different crystalline forms (Example 39k). One was crystallised from acetonitrile and had a melting point (melting onset) 108.5° C. This form will hereinafter be referred to as Form A. The other crystalline from described on page 176 of WO2007/007041 had a melting point (melting onset) of 113.8° C. This form will hereinafter be referred to as Form A'. The preparation of Form A is also described in the Example hereinafter. Form A and Form A' convert to the amorphous form in aqueous media. The amorphous form has a different solubility profile to the Form A. Stable crystalline forms that do not convert to other forms with different solubilities in aqueous media are preferred for pharmaceutical formulations.

DETAILED DESCRIPTION OF THE INVENTION

We have now surprisingly and unexpectedly discovered a second crystalline form of the Agent that is significantly more stable than Form A and Form A' and does not significantly convert to other forms in aqueous media. This form of the Agent will hereinafter be referred to as Form B.

Form B is characterised in providing at least one of the following 2-theta (2θ) values measured using CuKa radiation: 24.6° and 18.0°.

According to the present invention there is provided a crystalline form of the Agent, which has an X-ray powder diffraction pattern with at least one specific peak at about 2-theta=24.6°.

According to the present invention there is provided a crystalline form of the Agent, which has an X-ray powder diffraction pattern with at least one specific peak at about 2-theta=18.0°.

According to the present invention there is provided a crystalline form of the Agent, which has an X-ray powder diffraction pattern with at least two specific peaks at about 2-theta=24.6° and 18.0°.

According to the present invention there is provided a crystalline form of the Agent, which has an X-ray powder diffraction pattern with at least three specific peaks at about 2-theta=24.6°, 18.0° and 25.6°.

According to the present invention there is provided a crystalline form of the Agent, which has an X-ray powder diffraction pattern with at least four specific peaks at about 2-theta=24.6°, 18.0°, 25.6° and 23.8°.

According to the present invention there is provided a crystalline form of the Agent, which has an X-ray powder diffraction pattern with at least five specific peaks at about 2-theta=24.6°, 18.0°, 25.6°, 23.8° and 11.5°.

According to the present invention there is provided a crystalline form of the Agent, which has an X-ray powder diffraction pattern with at least six specific peaks at about 2-theta=24.6°, 18.0°, 25.6°, 23.8°, 11.5° and 9.1°.

According to the present invention there is provided a crystalline form of the Agent, which has an X-ray powder diffraction pattern with specific peaks at about 2-theta=24.6°, 18.0°, 25.6°, 23.8°, 11.5°, 9.1°, 22.9°, 15.9°, 14.9° and 22.0°.

According to the present invention there is provided a crystalline form of the Agent, which has an X-ray powder diffraction pattern substantially the same as the X-ray powder diffraction pattern shown in FIG. A.

According to the present invention there is provided a crystalline form of the Agent, which has an X-ray powder diffraction pattern with at least one specific peak at 2-theta=24.6° plus or minus 0.5° 2-theta.

According to the present invention there is provided a crystalline form of the Agent, which has an X-ray powder diffraction pattern with at least one specific peak at 2-theta=18.0° plus or minus 0.5° 2-theta.

According to the present invention there is provided a crystalline form of the Agent, which has an X-ray powder diffraction pattern with at least two specific peaks at 2-theta=24.6° and 18.0° wherein said values may be plus or minus 0.5° 2-theta.

According to the present invention there is provided a crystalline form of the Agent, which has an X-ray powder diffraction pattern with specific peaks at 2-theta=24.6°, 18.0°, 25.6°, 23.8°, 11.5°, 9.1°, 22.9°, 15.9°, 14.9° and 22.0° wherein said values may be plus or minus 0.5° 2-theta.

According to the present invention there is provided a crystalline form of the Agent, which has an X-ray powder diffraction pattern with at least one specific peak at 2-theta=24.6°.

According to the present invention there is provided a crystalline form of the Agent, which has an X-ray powder diffraction pattern with at least one specific peak at 2-theta=18.0°.

According to the present invention there is provided a crystalline form of the Agent, which has an X-ray powder diffraction pattern with at least two specific peaks at 2-theta=24.6° and 18.0°.

According to the present invention there is provided a crystalline form of the Agent, which has an X-ray powder diffraction pattern with specific peaks at 2-theta=24.6°, 18.0°, 25.6°, 23.8°, 11.5°, 9.1°, 22.9°, 15.9°, 14.9° and 22.0°.

According to the present invention there is provided a crystalline form of the Agent, which has an X-ray powder diffraction pattern substantially as shown in FIG. A.

Form B is characterised in providing an X-ray powder diffraction pattern, substantially as shown in FIG. A. The ten most prominent peaks are shown in Table A

TABLE A

Ten most Prominent X-Ray Powder Diffraction peaks for Form B

| Angle 2-Theta (2θ) | Intensity % | Relative Intensity |
|---|---|---|
| 24.573 | 100 | vs |
| 18.011 | 74.5 | vs |
| 25.577 | 61.4 | vs |
| 23.753 | 57.5 | vs |
| 11.510 | 43.1 | vs |
| 9.107 | 38.9 | vs |
| 22.885 | 35.7 | vs |
| 15.947 | 34.7 | vs |
| 14.872 | 33.4 | vs |
| 21.968 | 33.4 | vs | vs = very strong

Differential Scanning Calorimetry (DSC) analysis shows Form B is a high melting solid with an onset of melting at 136.8° C. and a peak at 142.5° C. (FIG. B).

When it is stated that the present invention relates to a crystalline form of the Agent in Form B, the degree of crystallinity is conveniently greater than about 60%. More conveniently, it is greater than about 80%. Particularly, it is greater than about 90%. More particularly, it is greater than about 95%. Most particularly, the degree of crystallinity is greater than about 98%.

Form B (IPA Form) provides X-ray powder diffraction patterns substantially the same as the X-ray powder diffraction patterns shown in FIG. A and has substantially the ten most prominent peaks (angle 2-theta values) shown in Table A. It will be understood that the 2-theta values of the X-ray powder diffraction pattern may vary slightly from one machine to another or from one sample to another, and so the values quoted are not to be construed as absolute.

It is known that an X-ray powder diffraction pattern may be obtained which has one or more measurement errors depending on measurement conditions (such as equipment or machine used). In particular, it is generally known that intensities in an X-ray powder diffraction pattern may fluctuate depending on measurement conditions. Therefore it should be understood that Form B (IPA Form) of the present invention is not limited to the crystals that provide X-ray powder diffraction patterns identical to the X-ray powder diffraction pattern shown in FIG. A, and any crystals providing X-ray powder diffraction patterns substantially the same as those shown in FIG. A fall within the scope of the present invention. A person skilled in the art of X-ray powder diffraction is able to judge the substantial identity of X-ray powder diffraction patterns.

Persons skilled in the art of X-ray powder diffraction will realise that the relative intensity of peaks can be affected by, for example, grains above 30 microns in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values. (Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures).

Generally, a measurement error of a diffraction angle in an X-ray powder diffractogram is about 5% or less, in particular plus or minus 0.5° 2-theta, and such degree of a measurement error should be taken into account when considering the X-ray powder diffraction pattern in FIG. A and when reading Table A. Furthermore, it should be understood that intensities might fluctuate depending on experimental conditions and sample preparation (preferred orientation).

As mentioned hereinabove, Form B is a more stable form of the compound of the Formula (I) than Form A. Competitive slurries of Form A and Form B in a range of solvents show that Form B is the most stable form. Form B also has a much higher melting endotherm.

Form B may be obtained by slurrying form A in isopropanol (propan-2-ol).

Therefore in a further aspect of the present invention is provided a process for the manufacture of Form B of a compound of formula (I), which comprises forming crystals from a saturated solution of compound of formula (I) in isopropanol.

Saturation of the solution with the Agent means addition of, for example the amorphous form to the sodium salt solution until the solution is saturated with respect to the amorphous form. Further amorphous form is added to maintain the saturation once crystallisation of Form B has started.

The process of the invention is conveniently carried out between 15 and 45° C., more conveniently at ambient temperature.

Form B may also be formed by seeding an isopropanol solution or slurry of Form A of the Agent, or by prolonged stirring of a suspension of the amorphous form.

The utility of the compound of the invention may be demonstrated by standard tests and clinical studies, including those described in International patent application publication number WO03/015774, which is hereby incorporated by reference.

A further feature of the invention is a pharmaceutical composition comprising Form B of the Agent, together with a pharmaceutically-acceptable diluent or carrier.

According to another aspect of the invention there is provided the use of a Form B of the Agent for use as a medicament.

According to another aspect of the invention there is provided Form B of the Agent for use as a medicament for treatment of a disease mediated through GLK, in particular type 2 diabetes.

Further according to the invention there is provided the use Form B of the Agent in the preparation of a medicament for treatment of a disease mediated through GLK, in particular type 2 diabetes.

The compound is suitably formulated as a pharmaceutical composition for use in this way.

According to another aspect of the present invention there is provided a method of treating GLK mediated diseases, especially diabetes, by administering an effective amount of Form B of the Agent to a mammal in need of such treatment.

Specific diseases which may be treated by a compound or composition of the invention include: blood glucose lowering in Type 2 Diabetes Mellitus without a serious risk of hypoglycaemia (and potential to treat type 1), dyslipidemia, obesity, insulin resistance, metabolic syndrome X, impaired glucose tolerance.

The GLK/GLKRP system can be described as a potential "Diabesity" target (of benefit in both Diabetes and Obesity). Thus, according to another aspect of the invention there is provided the use of a Form B of the Agent, in the preparation of a medicament for use in the combined treatment or prevention, particularly treatment of diabetes and obesity.

According to another aspect of the invention there is provided the use of Form B of the Agent in the preparation of a medicament for use in the treatment or prevention, particularly treatment of obesity.

According to another aspect of the invention there is provided Form B of the Agent for use as a medicament for treatment or prevention, particularly treatment of obesity.

According to a further aspect of the invention there is provided a method for the combined treatment of obesity and diabetes by administering an effective amount of Form B of the Agent, to a mammal in need of such treatment.

According to a further aspect of the invention there is provided a method for the treatment of obesity by administering an effective amount of Form B of the Agent to a mammal in need of such treatment.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing). Dosage forms suitable for oral use are preferred.

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound will naturally vary according to the nature and severity of the conditions, the age and sex of the animal or patient and the route of administration, according to well known principles of medicine.

In using a compound of the Form B for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

BRIEF DESCRIPTION OF THE DRAWINGS

FIG. A shows the x-ray powder diffraction pattern of Form B.
FIG. B shows the DSC thermogram of Form B.

EXAMPLES

In the following non-limiting Examples, unless otherwise stated:

(i) evaporations were carried out by rotary evaporation in vacuo and work-up procedures were carried out after removal of residual solids such as drying agents by filtration;

(ii) operations were carried out at room temperature, that is in the range 18-25° C. and under an atmosphere of an inert gas such as argon or nitrogen;

(iii) yields are given for illustration only and are not necessarily the maximum attainable;

(iv) the structures of the end-products of the Formula (I) were confirmed by nuclear (generally proton) magnetic resonance (NMR) with a field strength (for proton) of 300 MHz (generally using a Varian Gemini 2000) or 400 MHz (generally using a Bruker Avance DPX400), unless otherwise stated, and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(v) Purification by chromatography generally refers to flash column chromatography, on silica unless otherwise stated. Column chromatography was generally carried out using prepacked silica cartridges (from 4 g up to 400 g) such as Redisep™ (available, for example, from Presearch Ltd, Hitchin, Herts, UK) or Biotage (Biotage UK Ltd, Hertford, Herts, UK), eluted using a pump and fraction collector system. Purification by Solid Phase Extraction (SPE) methods generally refers to the use of chromatography cartridges packed with SPE materials such as ISOLUTE® SCX-2 columns (available, for example, From International Sorbent Technology Ltd, Dryffryn Business Park, Hengoed, Mid Glamorgan, UK);

(iv) Melting points were generally carried out by Differential Scanning Calorimetry (DSC). It will be understood that the onset and/or peak temperature values of the DSC may vary slightly from one machine to another, one method to another or from one sample to another, and so the values quoted are not to be construed as absolute. It will be appreciated that some samples may be solvates and that this may also affect melting points.

| Abbreviations | |
|---|---|
| DCM | dichloromethane |
| DSC | differential scanning calorimetry |
| XRPD | X-ray powder diffraction |

Example 1

Preparation of 3-{[5-(azetidin-1-ylcarbonyl)pyrazin-2-yl]oxy}-5-[(1-methylethyl)oxy]-N-1H-pyrazol-3-ylbenzamide—Form B The X-ray powder diffraction spectra for Form A showed the material to be crystalline. This material had a melting point of 108.5° C. (onset). In order to produce the second crystalline form, Form B, 200 mg of material was placed in a vial with a magnetic flea, and 2 ml of isopropanol (IPA) added. The vial was then sealed tightly with a cap. The slurry was then left to stir on a magnetic plate at ambient temperature (25° C.). After 3 days, the sample was removed from the plate, the cap taken off and the slurry left to dry under ambient conditions before it was analysed by XRPD and DSC. This form (Form B) was determined to be crystalline by XRPD and seen to be different to Form A. This material (Form B) had a melting point of 136.8° C. (onset).

Form A may be prepared as described in PCT/GB2006/002471 (WO2007/007041) or as follows:

3-{[5-(Azetidin-1-ylcarbonyl)pyrazin-2-yl]oxy}-5-[(1-methylethyl)oxy]-N-1H-pyrazol-3-ylbenzamide—Form A

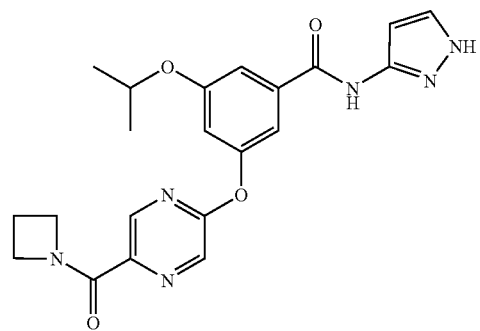

tert-Butyl 3-[(3-hydroxy-5-propan-2-yloxy-benzoyl)amino] pyrazole-1-carboxylate (56.3 g) was dissolved in acetonitrile (500 ml) and charged to a 3L fixed vessel. Potassium carbonate (325 mesh, 64.5 g) was added, followed by azetidin-1-yl-(5-chloropyrazin-2-yl)methanone (33.5 g) with an acetonitrile charge wash (100 ml). The mixture was stirred rapidly and warmed to 60° C. under nitrogen. Extra acetonitrile (250 ml) was added and the mixture stirred at 60° C. for 20 hours.

After cooling to room temperature the potassium carbonate was filtered off and the filtrate was concentrated under vacuum to remove the acetonitrile. The residual solution was poured into water (1500 ml) with stirring and the precipitated solid was filtered off. The solid was dissolved in dichloromethane (560 ml), washed with 1:1 brine/saturated sodium hydrogen carbonate (2×500 ml) and dried (MgSO$_4$). Trifluoroacetic acid (100 ml) was added and the solution was stirred at room temperature for 20 hours. The solvent was removed under vacuum and azeotroped with toluene. The residue was dissolved in ethyl acetate (500 ml) and washed with saturated sodium hydrogen carbonate (2×500 ml), brine (500 ml) dried (MgSO$_4$) and concentrated to leave a waxy solid (64 g). This was triturated with ethyl acetate (200 ml) at 45° C. for 2 hr. The solid was filtered off, washed with ethyl acetate and dried in a vacuum oven at 40° C. overnight to leave a solid (52 g). The crude solid was purified by flash chromatography on silica, eluting with methanol containing 2% ammonia in dichloromethane (0.5 to 6.5%) to afford the title compound (48.4 g).

The solid was dissolved in refluxing ethyl acetate (900 ml). Small amount of undissolved extraneous material remained. The solution was filtered whilst hot and cooled to 60° C., isohexane (250 ml) was added dropwise (at the end of the addition cloudiness remained). The slurry was cooled to 20° C. over approx 1 hour and then stirred at room temp for 20 hours. The slurry was filtered and washed with isohexane (2×200 ml). The solid was dried in a vacuum oven at 60° C. for 24 hours afford the title compound as form A (33.1 g). $^1$H NMR δ (400 MHz, CDCl$_3$) 1.36 (6H, d), 2.34-2.42 (2H, m), 4.25 (2H, t), 4.55-4.61 (1H, m), 4.68 (2H, t), 6.83 (1H, d), 7.25 (1H, t), 7.33-7.34 (1H, m), 7.39 (1H, d), 8.37 (1H, d), 8.80 (1H, d), 10.42 (1H, s).

Form B may also be prepared in a similar way using form A' instead of form A.

The starting materials were prepared as follows:

tert-Butyl 3-[(3-phenylmethoxy-5-propan-2-yloxy-benzoyl)amino]pyrazole-1-carboxylate

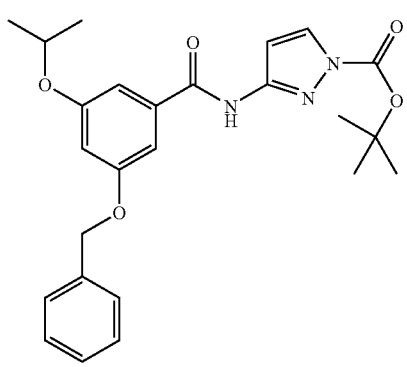

A solution of oxalyl chloride (76 ml) in dichloromethane (125 ml) was added dropwise to a slurry of 3-phenylmethoxy-5-propan-2-yloxy-benzoic acid (CAS no. 852520-53-7) (50 g) and dimethylformamide (1 ml) in dichloromethane (300 ml). The resulting solution was stirred at room temperature for 2 hours. The solvent was removed under vacuum and azeotroped with toluene (200 ml). The residue was dissolved in dry pyridine (100 ml). The mixture was added slowly to a mixture of tert-butyl 3-aminopyrazole-1-carboxylate (CAS no. 863504-84-1) (38.4 g) in dry pyridine (325 ml) under nitrogen over 5 minutes. The mixture was stirred at room temperature for 1 hour and solvent was removed under vacuum and azeotroped with toluene. The residue was partitioned between dichloromethane (500 ml) and water (500 ml) and the organic layer was washed with saturated sodium hydrogen carbonate (500 ml) and brine (500 ml) and dried (MgSO$_4$) and concentrated under vacuum, azeotroped twice with toluene to leave a residue which was purified by flash chromatography, eluting with 25-50% ethyl acetate in isohexane (25 to 50%) to afford the title compound (76.4 g).

tert-Butyl 3-[(3-hydroxy-5-propan-2-yloxy-benzoyl)amino]pyrazole-1-carboxylate

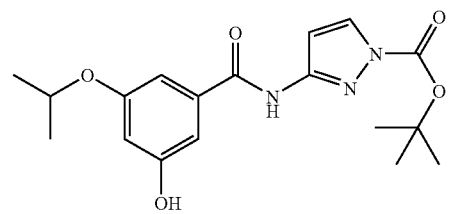

To a solution of tert-butyl 3-[(3-phenylmethoxy-5-propan-2-yloxy-benzoyl)amino]pyrazole-1-carboxylate (76.4 g) in methanol (764 ml) was added 10% palladium on carbon (7.6 g) and the resulting mixture was stirred under an atmosphere of hydrogen at a pressure of 5 bar for 20 hours. The catalyst was removed by filtration through Celite. The filtrate was concentrated under vacuum to leave a solid (66 g). This was purified by flash chromatography on silica, eluting with ethyl acetate in isohexane (10 to 70%) to give the title compound (56.4 g).

5-Chloropyrazine-2-carboxylic acid

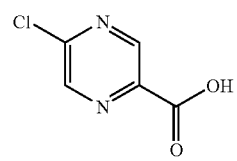

Methyl 5-chloropyrazine-2-carboxylate (CAS no. 33332-25-1)(345.1 g) was dissolved in DMF (1.73 l). Lithium chloride (423.9 g) was added and the mixture heated to 140° C. over one hour. The mixture was evaporated, and the residue dissolved in water (3.4 l) by continued stirring. The solution was acidified by addition of 2N HCl (900 ml) and extracted into ethyl acetate (5×1.73 l). The combined organic extracts were washed with water (2×900 ml), brine (900 ml), dried (MgSO₄), and evaporated to give the title compound (298.1 g). ¹H NMR δ (400.132 MHz, DMSO) 8.92 (d, 1H), 9.02 (d, 1H), 13.87 (s, 1H).

Azetidin-1-yl-(5-chloropyrazin-2-yl)methanone

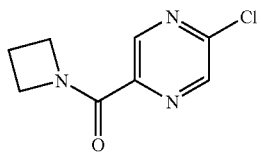

5-Chloropyrazine-2-carboxylic acid (277.4 g) was added to a solution of oxalyl chloride (186.5 ml) in dichloromethane (3.1 l) and the resulting mixture was stirred for 3 hours. The residue was dissolved in DCM (6.2 l), filtered and added to a solution of azetidine hydrochloride (CAS no. 36520-39-5) (180 g) and triethylamine (560 ml) in DCM (3.1 l). The mixture was stirred 10 minutes and solvent removed by evaporation. Residue partitioned between ethyl acetate (3.1 l) and water (3.1 l), extracted further into ethyl acetate (2×800 ml). The combined organic extracts were washed with water (3 l), brine (3 l), dried (MgSO₄) and evaporated. The residue was purified by flash chromatography on silica eluting with 50% ethyl acetate in isohexane to give the product (210 g). ¹H NMR δ (400 MHz, DMSO) 2.27-2.34 (m, 2H), 4.11 (t, 2H), 4.54 (t, 2H), 8.83 (d, 1H), 8.92 (d, 1H); m/z 198 (M+H)⁺.

Preparation of Form B by Seeding

To a sample of Form A (3.9 g, 9.3 mmol) was added isopropanol (3 mL). A sample of seed crystals of Form B prepared previously (20 mg) was added, and the resulting slurry was stirred at room temperature for 3 days. The solid was isolated by filtration and dried under vacuum (3.31 g, 85%). The DSC indicated complete conversion to the new form, melting point 136.4 (onset).

¹H NMR δ (400 MHz, CDCl₃) 1.36 (6H, d), 2.34-2.42 (2H, m), 4.25 (2H, t), 4.55-4.61 (1H, m), 4.68 (2H, t), 6.83 (1H, d), 7.25 (1H, t), 7.33-7.34 (1H, m), 7.39 (1H, d), 8.37 (1H, d), 8.80 (1H, d), 10.42 (1H, s).

X-Ray Powder Diffraction of Form B

TABLE B

| % Relative Intensity* | Definition |
|---|---|
| 25-100 | vs (very strong) |
| 10-25 | s (strong) |
| 3-10 | m (medium) |
| 1-3 | w (weak) |

*The relative intensities are derived from diffractograms measured with fixed slits Analytical Instrument: Siemens D5000. The X-ray powder diffraction spectra were determined by mounting a sample of the crystalline material on a Siemens single silicon crystal (SSC) wafer mount and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5406 angstroms. The collimated X-ray source was passed through an automatic variable divergence slit set at V20 and the reflected radiation directed through a 2 mm antiscatter slit and a 0.2 mm detector slit. The sample was exposed for 1 second per 0.02 degree 2-theta increment (continuous scan mode) over the range 2 degrees to 40 degrees 2-theta in theta-theta mode. The running time was 31 minutes and 41 seconds. The instrument was equipped with a scintillation counter as detector. Control and data capture was by means of a Dell Optiplex 686 NT 4.0 Workstation operating with Diffract+software. Persons skilled in the art of X-ray powder diffraction will realise that the relative intensity of peaks can be affected by, for example, grains above 30 microns in size and non-unitary aspect ratios that may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values.

Differential Scanning Calorimetry

Analytical Instrument: Mettler DSC820e. Typically less than 5 mg of material contained in a 40 μl aluminum pan fitted with a pierced lid was heated over the temperature range 25° C. to 325° C. at a constant heating rate of 10° C. per minute. A purge gas using nitrogen was used—flow rate 100 ml per minute.

The invention claimed is:

1. A crystalline form of the compound 3-{[5-(azetidin-1-ylcarbonyl)pyrazin-2-yl]oxy}-5-[(1-methylethyl)oxy]-N-1H-pyrazol-3-ylbenzamide having an X-ray powder diffraction pattern with peaks at least one of the following 2-theta values measured using CuKa radiation: 24.6° and 18.0°.

2. A crystalline form as claimed in claim 1 having an X-ray powder diffraction pattern with peaks at the following 2-theta values measured using CuKa radiation: 24.6° and 18.0°.

3. A crystalline form as claimed in claim 1 having an X-ray powder diffraction pattern with peaks at the following 2-theta values measured using CuKa radiation: 24.6°, 18.0° and 25.6°.

4. A crystalline form as claimed in claim 1 having an X-ray powder diffraction pattern with peaks at the following 2-theta values measured using CuKa radiation: 24.6°, 18.0°, 25.6° and 23.8°.

5. A crystalline form as claimed in claim 1 having an X-ray powder diffraction pattern with peaks at the following 2-theta values measured using CuKa radiation: 24.6°, 18.0°, 25.6°, 23.8° and 11.5°.

6. A crystalline form as claimed in claim 1 having an X-ray powder diffraction pattern with peaks at the following 2-theta values measured using CuKa radiation: 24.6°, 18.0°, 25.6°, 23.8°, 11.5° and 9.1°.

7. A crystalline form as claimed in claim 1 having an X-ray diffraction pattern substantially the same as the X-ray diffraction pattern shown in FIG. A.

8. A crystalline form of the compound 3-{[5-(azetidin-1-ylcarbonyl)pyrazin-2-yl]oxy}-5-[(1-methylethyl)oxy]-N-1H-pyrazol-3-ylbenzamide having a melting point of about 136.8° C. (onset).

9. A pharmaceutical composition comprising a crystalline form as claimed in claim 1, together with a pharmaceutically acceptable carrier.

* * * * *